(12) United States Patent
Revivo

(10) Patent No.: US 6,776,995 B1
(45) Date of Patent: Aug. 17, 2004

(54) SOUFFLE FACIAL AND BODY SCRUB

(76) Inventor: Rina Revivo, 14936 Camarillo St., Sherman Oaks, CA (US) 91403

( * ) Notice: Subject to any disclaimer, the term of this patent is extended or adjusted under 35 U.S.C. 154(b) by 113 days.

(21) Appl. No.: 10/183,587

(22) Filed: Jun. 26, 2002

Related U.S. Application Data

(60) Provisional application No. 60/383,895, filed on May 28, 2002.

(51) Int. Cl.$^7$ ................................................. A61K 7/50
(52) U.S. Cl. .................. 424/402; 424/70.1; 424/70.19; 424/70.21
(58) Field of Search ................................ 424/401, 402, 424/70.1, 70.19, 70.22, 489; 514/844, 846

(56) References Cited

U.S. PATENT DOCUMENTS

| | | |
|---|---|---|
| 4,776,970 A | 10/1988 | Hayashi |
| 5,534,265 A | 7/1996 | Fowler |
| 5,558,855 A | 9/1996 | Quay |
| 5,595,723 A | 1/1997 | Quay |
| 5,658,577 A | 8/1997 | Fowler |
| 5,707,607 A | 1/1998 | Quay |
| 5,876,696 A | 3/1999 | Quay |
| 6,306,805 B1 | 10/2001 | Bratescu |
| 6,338,855 B1 | 1/2002 | Albacarys |

FOREIGN PATENT DOCUMENTS

| | | | | |
|---|---|---|---|---|
| EP | 8711699.2 | 8/1987 | | |
| EP | 93303880.4 | 5/1993 | | |
| WO | PCT/US95/10485 | 8/1995 | | |
| WO | PCT/US99/10405 | 5/1999 | | |
| WO | WO 9958106 A1 | * | 11/1999 | ............ A61K/7/50 |

* cited by examiner

Primary Examiner—Thurman K. Page
Assistant Examiner—Micah-Paul Young
(74) Attorney, Agent, or Firm—Thomas I. Rozsa; Tony D. Chen

(57) ABSTRACT

The present invention is a souffle facial and body scrub which has enhanced properties to deep clean skin, exfoliate dead skin cells in an efficient manner, and at the same time not damage sensitive skin, especially oh a woman's face. It is an object of the present invention to provide an improved facial and body scrub which will provide deep cleaning action to cleanse skin pores in an efficient manner and also to exfoliate skin in an efficient manner. It is a further object of the present invention to provide an improved exfoliating facial and body scrub which although effective for cleaning and exfoliating skin, is not so abrasive as to create any damage to sensitive skin areas, especially on a woman's face. It is a further object of the present invention to provide a cost efficient combination of elements and process for creating an improved facial and body scrub.

11 Claims, No Drawings

SOUFFLE FACIAL AND BODY SCRUB

This application claims the benefit of Provisional Ser. No. 60/383,895, filed May 28, 2002.

BACKGROUND OF THE INVENTION

1. Field of the Invention

The present invention generally relates to cosmetic cleansing products and in particular, to cosmetics products which are used to both clean and exfoliate dead skin cells from the face and other parts of the body such as the hands, arms, torso, back and legs.

2. Description of the Prior Art

The following prior art references are found to be relevant in the area of the present invention:

1. U.S. Pat. No. 4,776,970 issued to Hayashi on Oct. 11, 1988 for "Lubricant For Use In Parer Coating And Method For Producing The Same" (hereafter the "Hayashi Patent");

2. U.S. Pat. No. 5,534,265 issued to Fowler on Jul. 9, 1996 for "Thickened Nonabrasive Personal Cleansing Compositions" (hereafter the "Fowler Patent");

3. U.S. Pat. No. 5,558,855 issued to Quay on Sep. 24, 1996 for "Phase Shift Colloids As Ultrasound Contrast Agents" (hereafter the "'855 Quay Patent");

4. U.S. Pat. No. 5,595,723 issued to Quay on Jan. 21, 1997 for "Method For Preparing Storage Stable Colloids" (hereafter the "'723 Quay Patent");

5. U.S. Pat. No. 5,658,577 issued to Fowler on Aug. 19, 1997 for "Thickened Nonabrasive Personal Cleansing Compositions" (hereafter the "Fowler Patent");

6. U.S. Pat. No. 5,707,607 issued to Quay on Jan. 13, 1998 for "Phase Shift Colloids As Ultrasound Contrast Agents" (hereafter the "'607 Quay Patent");

7. U.S. Pat. No. 5,876,696 issued to Quay on Mar. 2, 1999 for "Composition Comprising A Fluorine Containing Surfactant And Perfluoropentane For Ultrasound" (hereafter the "'696 Quay Patent");

8. U.S. Pat. No. 6,306,805 B1 issued to Bratescu on Oct. 23, 2001 for "Shampoo And Body Wash Composition Comprising Ternary Surfactant Blends Of Cationic, Anionic, And Bridging Surfactants And methods Of Preparing Same" (hereafter the "Bratescu Patent");

9. U.S. Pat. No. 6,338,855 B1 issued to Albacarys on Jan. 15, 2002 for "Cleansing Articles For Skin And/Or Hair Which Also Deposit Skin Care Actives" (hereafter the "Albacarys Patent");

10. PCT Application No. PCT/US99/10405 filed on May 15, 1999 by Damon Dalrymple for "Clear Personal Care Formulations Containing Quaternary Ammonium Compounds And Other Nitrogen-Containing Compounds" (hereafter the "Dalrymple PCT Application"). 11. PCT Application No. PCT/US95/10485 filed on Aug. 15, 1995 by Timothy Fowler for "Personal Cleansing Compositions" (hereafter the "Fowler PCT Application").

12. EPO Application No. 93303880.4 filed on May 19, 1993 by Robert Stanley Lee for "Exfoliant Composition" (hereafter the "Lee European Application").

13. EPO Application No. 87111699.2 filed on Aug. 12, 1987 by Yukio Ozaki for "Scrubbing Agent And Process For Producing The Same" (hereafter the "Ozaki European Application").

The Hayashi Patent discloses a lubricant for use in paper coating and method for producing the same. The purpose of citing the Hayashi Patent is that it discloses a lubricant that contains both sodium polyacrylate and ethylhexyl stearate. However, the purpose and use of this innovation is completely different from the present invention.

The '265 Fowler Patent discloses a non-abrasive thickened aqueous-based personal cleansing composition. The compositions utilize insoluble micronized cleansing particles but do not use ethylhexyl stearate.

The '855 Quay Patent is a phase shift colloidal as ultrasound contrast agent which discloses agents for enhancing the contrast in a diagnostic ultrasound procedure.

The '723 Quay Patent discloses a method for preparing storage stable colloids, again used with ultrasound.

The '607 Quay Patent also discloses a method for preparing storage stable colloids, again used with ultrasound.

The '696 Quay Patent also discloses a method for preparing storage stable colloids, again used with ultrasound.

The '577 Fowler Patent relates to nonabrasive thickened aqueous-based personal cleansing compositions. These compositions utilize insoluble micronized cleansing particles of the fine particle size that are not tactiley perceived by the user during the cleansing process and which provide improved cleansing performance. This patent does not show the use of ethylhexyl stearate.

The Bratescu Patent discloses a shampoo and body wash composition comprising ternary surfactant blends of cationic, anionic, and bridging surfactants and methods of preparing same. This patent does not disclose the use of ethylhexyl stearate.

The Albacarys Patent discloses a substantially dry, disposable, personal cleansing article useful for both cleansing the skin or hair and delivering skin care actives onto the skin or hair. The article comprises a water insoluble substrate, a lathering surfactant, and a skin care active component. This patent does not disclose the use of ethylhexyl stearate.

The PCT Application to Dalrymple discloses a personal care formulation.

The Fowler PCT Application is comparable to the United States case of Fowler.

The Lee European Application discloses an exfoliant composition.

Finally, the Ozaki European Application also discloses a scrubbing agent.

While exfoliating compounds have already been developed in the prior art, many exfoliating compounds either do not provide a sufficiently deep cleansing action or alternatively, may be sufficiently abrasive to damage sensitive skin especially on a woman's face. Therefore, there is a significant need for an improved facial and body scrub which can deep clean skin tissue and also exfoliate dead skin cells while at the same time not damaging sensitive skin.

SUMMARY OF THE INVENTION

The present invention is a souffle facial and body scrub which has enhanced properties to deep clean skin, exfoliate dead skin cells in an efficient manner, and at the same time not damage sensitive skin, especially on a woman's face.

It is an object of the present invention to provide an improved facial and body scrub which acts as a souffle in that it creates a blown up foam which will provide deep cleaning action to cleanse skin pores in an efficient manner and also to exfoliate skin in an efficient manner.

It is a further object of the present invention to provide a souffle exfoliating facial and body scrub which although effective for cleaning and exfoliating skin, is not so abrasive as to create any damage to sensitive skin areas, especially on a woman's face.

It is a further object of the present invention to provide a cost efficient combination of elements and process for creating an improved facial and body scrub.

Further novel features and other objects of the present invention will become apparent from the following detailed description, discussion and the appended claims, taken in conjunction with the drawings.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The preferred embodiment of the present invention consists of a combination of six primary elements which are as follows: (1) Sodium Laureth Sulfate (hereafter defined as "SLES"); (2) Cocamidopropyl Betaine; (3) Fine Salt or Coarse Salt; (4) vanilla fragrance RR79226; (5) Sodium Polyacrylate, Ethylhexyl Stearate and Trideceth-6 which are hereafter referred to as "Rheocare ATH"; (6) and an additional addition of Fine Salt.

While the preferred embodiment of the present invention can obtain various ranges of the chemical compounds as discussed above, the preferred combination of the chemical compounds to create the souffle facial and body scrub can be set forth in the following chart:

CHART 1

| DESCRIPTION OF CHEMICAL | FORMULA % | WEIGHT (kg) | AMOUNT NEEDED |
|---|---|---|---|
| SLES | 37.56 | 11.27 | 11.27 kg. |
| Cocamidopropyl Betaine | 10.99 | 3.30 | 3.30 kg. |
| Fine Salt or Coarse Salt | 30.53 | 9.16 | 9.16 kg. |
| Vanilla Fragrance RR79226 | 1.83 | 0.55 | 549.00 g. |
| Rheocare ATH | 3.82 | 1.15 | 1.15 kg. |
| Fine Salt | 15.27 | 4.58 | 4.58 kg. |
| Total: | 100.00% | 30.00 | |

While the above-referenced percentages are the preferred embodiment of the present invention, it will be appreciated that the chemical formulations can also be in the following ranges to have an operative product:

CHART 2

DESCRIPTION OF CHEMICAL AND FORMULA BY PERCENTAGE

| DESCRIPTION OF CHEMICAL | FORMULA % |
|---|---|
| SLES | 20–50 |
| Cocamidopropyl Betaine | 5–15 |
| Fine Salt or Coarse Salt | 25–40 |
| Vanilla Fragrance RR79226 | 0.5–3.0 |
| Rheocare ATH | 0.5–5.0 |

CHART 2-continued

DESCRIPTION OF CHEMICAL AND FORMULA BY PERCENTAGE

| DESCRIPTION OF CHEMICAL | FORMULA % | |
|---|---|---|
| Fine Salt | 5–20 | |
| Total: | 100.00% | 30.00 |

Referring to CHART 2 wherein the percentage of Sodium Laureth Sulfate can range from 20 percent to 50 percent, for those combinations where the percentage is below 37.56 percent, the remaining percentage of chemicals are proportionately increased, and for those combinations where the percentage is above 37.56 percent, the remaining percentage of chemicals are proportionately decreased.

Further referring to CHART 2 wherein the percentage of Cocamidopropyl Betaine can range from 5 percent to 15 percent, for those combinations where the percentage is below 10.99 percent, the remaining percentages of chemicals are proportionately increased, and for those combinations where the percentage is above 10.99 percent, the remaining percentage of chemicals are proportionately decreased.

Further referring to CHART 2 wherein the first percentage of Fine Salt or Coarse Salt can range from 25% to 40%, for those combinations wherein the percentage is below 30.53 percent, the remaining percentages of chemicals are proportionately increased, and for those combinations where the percentage is above 30.53 percent, the remaining percentage of chemicals are proportionately decreased.

Further referring to CHART 2 wherein the percentage of Vanilla Fragrance can range from 0.5 percent to 3 percent, for those combinations wherein the percentage is below 1.83 percent, the remaining percentages of the chemicals are proportionately increased, and for those combinations where the percentage is above 1.83 percent, the remaining percentage of chemicals are proportionately decreased.

Further referring to CHART 2 wherein the percentage of combination of Sodium Polyacrylate, Ethyhexyl Stearate and Trideceth-6 can range from 0.5 percent to 5 percent, for those combinations where the percentage is below 3.82 percent, the remaining percentage of chemicals are proportionately increased, and for those combinations where the percentage is above 3.82 percent, the remaining percentage of chemicals are proportionately decreased.

Further referring to CHART 2 wherein the percentage of Fine Salt in the last chemical is between 5 percent and 20 percent, for those combinations where the percentage is below 15.27 percent, the remaining percentage of chemicals are proportionately increased, and for those combinations where the percentage is above 15.27 percent, the remaining percentage of chemicals are proportionately decreased.

The compounding procedure for the above-referenced chemicals is as follows: Step 1. In a clean, sanitized container, combine SLES and Cocamidopropyl Betaine. Mix thoroughly until thick. The mixing time is approximately 5–10 minutes. After Step 1 for Step 2, slowly add fine or Coarse Salt. Continue the mixing until the batch is well mixed. The approximate period of time to mix the batch is 10–20 minutes. Step 3 is to slowly add the Vanilla Fragrance. Continue mixing until the batch is thicker. The appropriate mixing time is 10–20 minutes. In Step 4 add the Rheocare ATH with continuous mixing. This time the batch will slowly become thicker. The appropriate mixing time is 20–30 minutes. For Step 5, finally, add the second amount of Fine Salt and continue to mix well. The total mixing time for Step 5 is 10–20 minutes.

After the above items are mixed, the solution is ready for bottling. Through use of the present invention and the unique compounds in combination as set forth above, the present invention creates a vastly improved facial and body scrub with the enhanced properties as discussed above.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A souffle facial and body scrub, comprising:
   a. 20.00 percent to 50.00 percent sodium laureth sulfate;
   b. 5.00 percent to 10.00 percent cocamidopropyl betaine;
   c. 25.00 percent to 40.00 percent salt;
   d. 0.5 percent to 3.00 percent vanilla fragrance;
   e. 0.5 percent to 5 percent combination of sodium polyacrylate, ethylhexyl stearate and trideceth-6; and
   f. 5.00 percent to 20.00 percent fine salt.

2. The souffle facial and body scrub as defined in claim 1, wherein the initial 25.00 percent to 40.00 percent salt in element "c" is fine salt.

3. The souffle facial and body scrub as defined in claim 1, wherein the initial 25.00 percent to 40.00 percent in element "c" is coarse salt.

4. The souffle facial and body scrub as defined in claim 1, wherein the vanilla fragrance is RR79226.

5. A souffle facial and body scrub, comprising:
   a. 37.56 percent sodium laureth sulfate;
   b. 10.99 percent cocamidopropyl betaine;
   c. 30.53 percent salt;
   d. 1.83 percent vanilla fragrance;
   e. 3.82 percent combination of sodium polyacrylate, ethylexyl stearate and trideceth-6; and
   f. additional 15.27 percent fine salt.

6. The souffle facial and body scrub as defined in claim 4, wherein the initial 30.53 percent salt in element "c" is fine salt.

7. The souffle facial and body scrub as defined in claim 4, wherein the initial 30.53 percent salt in element "c" is coarse salt.

8. The souffle facial and body scrub as defined in claim 4, wherein the vanilla fragrance is RR79226.

9. The souffle facial and body scrub wherein the proportion of chemicals used to create 30 kg. of the souffle facial and body scrub comprise:
   a. 11.27 kg. of sodium laureth sulfate;
   b. 3.30 kg. of cocamidopropyl betaine;
   c. 9.16 kg. of salt;
   d. 0.55 kg. of vanilla fragrance;
   e. 15 kg. of the combination of sodium polyacrylate, ethylhexyl stearate and trideceth-6; and
   f. adding an additional 4.58 kg. of fine salt.

10. A process for creating a souffle facial and body scrub, comprising:
    a. cleaning and sanitizing a container;
    b. combining 37.50 percent sodium laureth sulfate and 10.99 percent cocamidopropyl betaine and mixing thoroughly for five to ten minutes;
    c. slowly adding 30.53 percent salt to the mixture and continue mixing for 10 to 20 minutes;
    d. slowly adding 1.83 percent vanilla fragrance to the mixture and continue mixing for 10 to 20 minutes;,
    e. slowly adding 3.82 percent combination of sodium polyacrylate, ethylhexyl stearate and trideceth-6 and mixing for 20 to 30 minutes; and
    f. adding an additional 15.27 percent fine salt to the mixture and mixing for 10 to 20 minutes.

11. A process for creating a souffle facial and body scrub, comprising:
    a. cleaning and sanitizing a container;
    b. combining from 20 to 50 percent sodium laureth sulfate and from 5 to 15 percent cocamidopropyl betaine and mixing thoroughly for five to ten minutes;
    c. slowly adding 25 percent to 40 percent salt to the mixture and continue mixing for 10 to 20 minutes;
    d. slowly adding from 0.5 percent to 3 percent vanilla fragrance to the mixture and continue mixing for 10 to 20 minutes;
    e. slowly adding from 0.5 percent to 5.0 percent of the combination of sodium polyacrylate, ethylhexyl stearate and Trideceth-6 to the mixture and mixing for 20 to 30 minutes; and
    f. adding an additional from 5 percent to 20 percent fine salt to the mixture and mixing for 10 to 20 minutes.

* * * * *